(12) United States Patent
Sias et al.

(10) Patent No.: US 6,343,425 B1
(45) Date of Patent: Feb. 5, 2002

(54) MEASUREMENT AND CLEANING OF ELASTOMERIC ARTICLES HAVING PARTICULATE ADHERED THERETO

(75) Inventors: Ralph M. Sias, Oceanside; Heath E. Sias, San Marcos, both of CA (US)

(73) Assignee: Intecon Systems, Inc., Carlsbad, CA (US)

( * ) Notice: Subject to any disclaimer, the term of this patent is extended or adjusted under 35 U.S.C. 154(b) by 0 days.

(21) Appl. No.: 09/306,519

(22) Filed: May 6, 1999

(51) Int. Cl.⁷ .............................. A61L 2/20; A61L 2/14
(52) U.S. Cl. .............................. 34/389; 422/23; 422/29
(58) Field of Search ............................ 34/104, 105, 106, 34/107, 191, 380, 389, 415, 565, 567, 572, 573, 574; 134/1.1; 422/22, 23, 28, 29

(56) References Cited

U.S. PATENT DOCUMENTS

| | | | |
|---|---|---|---|
| 3,992,221 A | * 11/1976 | Homsy et al. | ................. 134/16 |
| 4,366,125 A | * 12/1982 | Kodera et al. | ............... 422/295 |
| 4,643,876 A | * 2/1987 | Jacobs et al. | ................. 422/23 |
| 4,817,800 A | 4/1989 | Williams et al. | |
| 5,058,785 A | * 10/1991 | Rich et al. | .................... 223/111 |
| 5,084,239 A | * 1/1992 | Moulton et al. | ............... 422/22 |
| 5,115,166 A | * 5/1992 | Campbell | .............. 315/111.21 |
| 5,178,829 A | * 1/1993 | Moulton et al. | ............... 422/23 |
| 5,184,046 A | * 2/1993 | Campbell | .............. 315/111.21 |
| 5,604,993 A | * 2/1997 | Auckerman | ................... 34/104 |
| 5,667,753 A | 9/1997 | Jacobs et al. | |
| 5,876,666 A | 3/1999 | Lin et al. | |
| 5,882,611 A | 3/1999 | Williams et al. | |
| 5,942,438 A | 8/1999 | Antonoplos et al. | |
| 6,062,976 A | * 5/2000 | De Guzman | ................ 454/187 |

* cited by examiner

Primary Examiner—Denise L. Esquivel
Assistant Examiner—Greg T. Warder
(74) Attorney, Agent, or Firm—Gregory Garmong

(57) ABSTRACT

An apparatus for processing an elastomeric article such as a glove includes an enclosure having a gas-filled interior, a support that receives the elastomeric article thereon and supports the elastomeric article within the enclosure, and a source of a gaseous cleaning agent which introduces a gaseous flow of the gaseous cleaning agent into the interior of the enclosure to contact the elastomeric article. The cleaning agent dislodges particulate contaminant from the elastomeric article and entrains the particulate contaminant in the gaseous flow as it passes by the elastomeric article. The source of the gaseous cleaning agent comprises a nebulizer source of a vaporized cleaning material, and a weakly ionized plasma source disposed within the interior of the enclosure and proximate to the article support location to create a weakly ionized plasma in the ambient atmosphere adjacent to the article support location. An exhaust port is positioned to receive the gaseous flow after it has passed by the elastomeric article, and a particle counter monitors the particles in the gaseous flow after it has passed by the elastomeric article. A microorganism sterilizer may be disposed within the interior of the enclosure and proximate to the article support location, to sterilize the elastomeric article.

20 Claims, 5 Drawing Sheets

MEASUREMENT AND CLEANING OF ELASTOMERIC ARTICLES HAVING PARTICULATE ADHERED THERETO

BACKGROUND OF THE INVENTION

This invention relates to the measurement of particulate adhered to elastomeric articles such as gloves, and the cleaning of the particulate from the articles.

Electronic devices such as microcircuits are fabricated and assembled inside clean rooms. Any particulate matter in the air may come to rest on the electronic devices, causing electrical shorts and otherwise rendering the devices inoperable. The air entering the clean room is therefore filtered to remove the airborne particulate matter. However, such filtering is not entirely without adverse consequences, inasmuch as it increases the static electricity in the clean room, which in turn tends to cause any airborne particulate to adhere to the electronic devices.

The workers in the clean room wear elastomeric gloves made of natural latex or synthetic elastomers to prevent contact of the skin of their hands to the electronic devices. The gloves are cleaned and packaged by glove manufacturers or laundries, but become contaminated with particles during shipping and storage. Elastomeric gloves are subject to surface hardening and microcracking. The microcracking allows particulate matter to be created and/or trapped at the microcracks. The particulate matter may later detach from the microcracks and surfaces of the gloves, and thence possibly reach the surfaces of the electronic devices.

The workers therefore change their gloves on a regularly scheduled basis, typically about every 30–60 minutes, whether or not the gloves have become contaminated with particulate matter. The regular changing of the gloves is meant to ensure that particulate-contaminated gloves are not used in the clean room operations. To change gloves, the workers leave the clean room, go to a donning room, remove the old gloves, don new gloves, and return to the clean room to work. This changing of the gloves typically entails 5–10 minutes of lost labor per hour for each worker.

Many electronic device fabrication processes performed inside clean rooms experience high scrap rates (i.e., low product yields) in part because of particulate contamination from items such as the gloves worn by the workers. The regular changing of the gloves in the clean room represents a significant addition to the cost of the electronic devices, both in the cost of the multiple pairs of gloves worn by the workers and in the lost labor time. However, experience has shown that the failure to change the gloves on this regular schedule results in significantly reduced product yields in the manufacturing operation due to particle contamination of the electronic devices. Current technology does not allow frequent testing and correlation of glove cleanliness to product yields.

Medical and dental personnel face a similar problem in their need to change elastomeric gloves on a regular basis. Even when working on a single patient, the medical and dental personnel must often change gloves several times, to avoid contamination of machinery and instruments.

There is a need to reduce the costs associated with the regular changing of gloves in clean room, medical, laboratory and other environments where particulate contamination must be avoided. The present invention fulfills this need, and further provides related advantages.

SUMMARY OF THE INVENTION

The present invention provides an apparatus and method for measuring the particulate content found on the surfaces of elastomeric articles such as gloves, and for reducing the particulate content to acceptable levels in the event that they are too high. The apparatus may be readily used in clean room, medical, laboratory, and other environments. The approach of the invention reduces the need to change gloves on a regular basis or, alternatively, increases the time between required changing of the gloves. The apparatus may also be used to monitor the number of times each worker changes gloves, and to correlate the changing of gloves with manufacturing yields. It also may be used to sterilize the glove of life forms, where sterilization is important such as in a medical or laboratory setting.

In accordance with the invention, an apparatus for processing an elastomeric article comprises an enclosure having a gas-filled interior, a support that supports the elastomeric article within the enclosure at an article support location, and a source of a gaseous cleaning agent operable to introduce a gaseous flow of the gaseous cleaning agent into the interior of the enclosure to flow past the article support location and to contact the elastomeric article. The cleaning agent is operable to dislodge a particulate contaminant from the elastomeric article and entrain the particulate contaminant in the gaseous flow as it passes by the elastomeric article. An exhaust port is positioned to receive the gaseous flow after it has passed by the elastomeric article. A particle counter measures particles in the gaseous flow after it has passed by the elastomeric article, and preferably after it has passed through the exhaust port.

The source of the gaseous cleaning agent desirably comprises a source of a vaporized cleaning material, such as nebulized EDTA, isopropyl alcohol, oxalic acid, or hydrogen peroxide, and a weakly ionized plasma source disposed within the interior of the enclosure and proximate to the article support to create a weakly ionized plasma in the ambient atmosphere adjacent to the article support. The weakly ionized plasma is of relatively low ionization energy so that the plasma does not harm the elastomeric article or a human being who may be wearing the elastomeric article during processing.

The elastomeric article and/or the gaseous cleaning agent may optionally be mechanically pressure pulsed during the processing. The pulsing action further aids in dislodging particulate from the elastomeric article.

The particulate matter is dislodged from the elastomer by the combined action of the vaporized cleaning material and the weakly ionized plasma source, and optionally by the mechanical pulsing. The particulate is entrained into the gas flow, and flows out of the enclosure through the exhaust port. The particle counter measures the amount of particulate in the gas flow, as a measure of the particulate on the elastomeric article initially and also during and after processing. If the processing successfully reduces the particulate content to an acceptable level, the elastomeric article may be placed back into service. The particle counter also allows the automatic recording of the time and results of particle tests for product scrap correlation. Such recording may be done on any data acquisition system such as a personal computer. In the context of an elastomeric glove, the glove may be reused, and the worker does not need to change gloves.

The removal of particulate matter is sufficient for many situations. In others, such as medical and laboratory facilities, it is also necessary to sterilize the elastomeric article by removal or destruction of living microorganisms. In that case, the enclosure may also be provided with a microorganism sterilizer disposed within the interior of the enclosure and proximate to the article support location.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
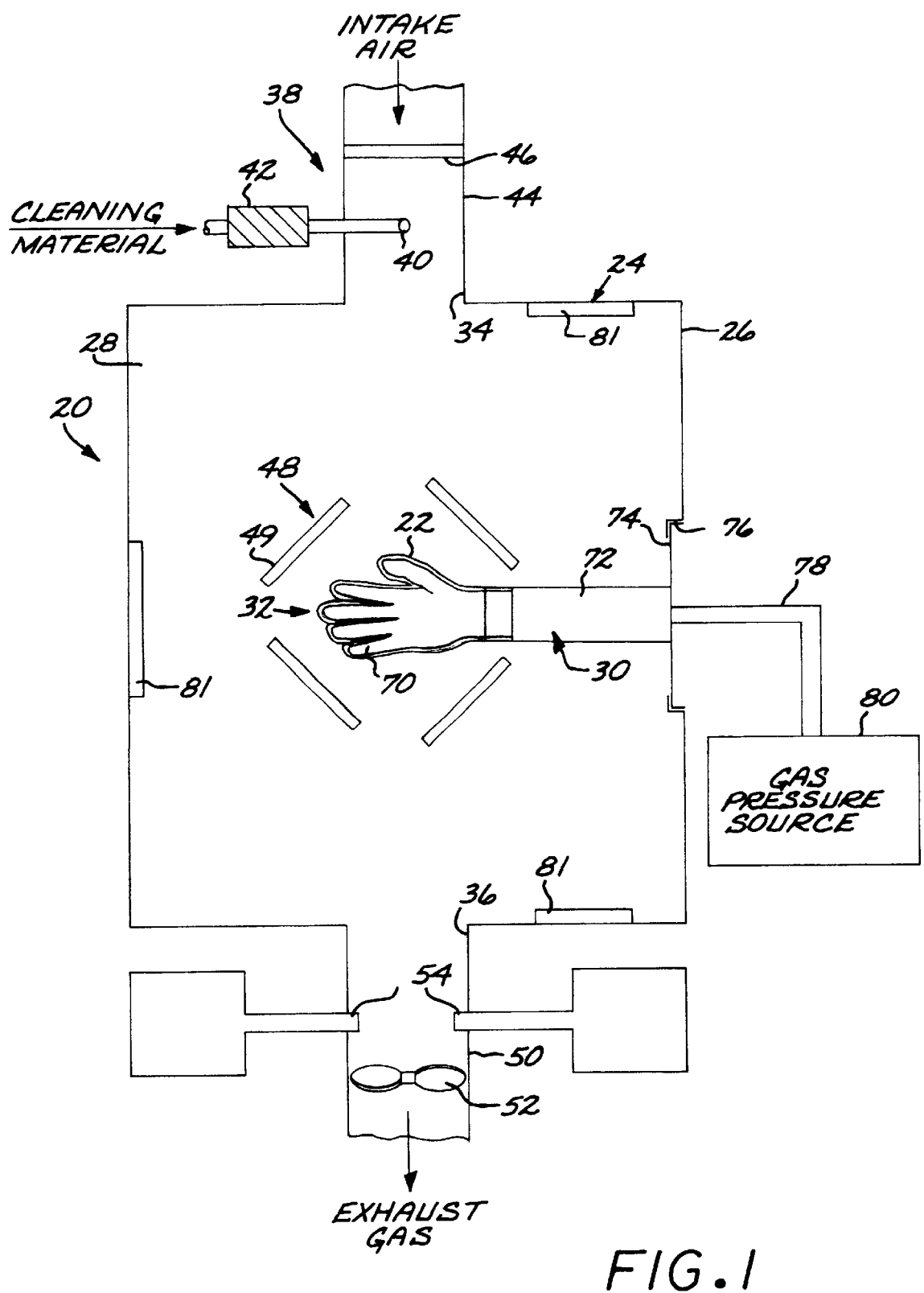
FIG. 1 is a schematic depiction of an apparatus according to a first embodiment of the invention.

FIG. 1 illustrates an apparatus 20 for processing an elastomeric article 22, in this case a preferred elastomeric glove. The processing of a glove article is presently preferred, but the present invention is operable with other types of articles as well. In the present application, "processing" encompasses both measuring the properties of the article, and/or modifying the article, as by cleaning the article, and/or performing correlations of the results of the measuring with other information.

The apparatus 20 includes an enclosure 24 having walls 26. An interior 28 of the enclosure 24 is gas filled, as distinct from liquid filled. The present approach does not immerse the article into a liquid, which facilitates the measurements, cleaning, and subsequent use of the article.

A support 30 supports the article 22 at an article support location 32. The article support location 32 is generally positioned intermediate between an intake port 34 and an exhaust port 36, but it need not be positioned at a precise location therebetween. In the embodiment of FIG. 1, the support 30 includes a rigid skeleton 70, made of an electrical nonconductor such as a plastic, which slides inside the article 22, in this case the glove to be processed. The skeleton 30 allows gaseous communication between the interior of the skeleton and the adjacent interior surface of the article 22, so that the article may be pressure pulsed, as described subsequently. The skeleton 70 is supported on a tubular support arm 72, with a closure 74 at the end remote from the skeleton 70. The closure 74 closes and seals an access port 76 in the wall 26 of the enclosure 24.

A gas pressure line 78 communicates at one end with the interior of the support arm 72 through an opening in the closure 74, and at the other end with a gas pressure source 80 that produces a gas pressure of from about 2 inches to about 15 inches of water. The thicker the wall of the article 22, the higher the pressure that is required. The gas pressure source 80 may deliver a static pressure, or it may deliver a dynamically varying pressure. Studies performed by the inventors have shown that accelerated and increased dislodging of particulate contaminant from the article 22 is attained by pulsing the gas pressure source 80, and thence the pressure within the article 22, preferably at a frequency of from about 20 to about 2000 Hertz. In these studies, the pulsing was provided by a commercial low-acoustic-range transducer communicating with the gas within the gas pressure source 80 and thence with the interior surface of the article 22 on the skeleton 70. The transducer membrane was driven by either a sine wave or a square wave in the indicated frequency range, with an output total amplitude variation of about 9.9 millimeters one way. Similar results may be obtained by applying low-acoustic-range pulsing to the gaseous environment within the enclosure 24, so that the article 22 is pulsed exteriorly, as with one or more sonic sources 81 communicating with the interior of the enclosure 24 and operating in a manner like that described above for the pulsing of the gas pressure source 80.

In operation, with the closure 74 removed from the port 76 and the support 30 easily accessible outside of the enclosure 24, the glove article 22 is placed over the skeleton 70, and sealed to the support arm 72. The support 30 is then inserted into the enclosure 24 so that the closure 74 fits into the port 76 and seals it. The skeleton 70 and support arm 72 are dimensioned such that the article 22 is thereby positioned in the article support location 32. The gas pressure source 80 is operated to inflate the glove article 22 slightly. The combination of the rigid skeleton 70 and the inflation pressure hold the glove article 22 at the article support location 32. The particular support 30 described herein is adapted for processing a glove article, the preferred embodiment, and other designs of supports may be used for other types of articles.

A source 38 of a gaseous cleaning agent is provided in the interior 28 of the enclosure 24. The source 38 of the gaseous cleaning agent is operable to introduce a gaseous flow of the gaseous cleaning agent into the interior 28 of the enclosure 24 to flow past the article support location 32 and to contact the elastomeric article 22 at that article support location 32.

Figure 2:
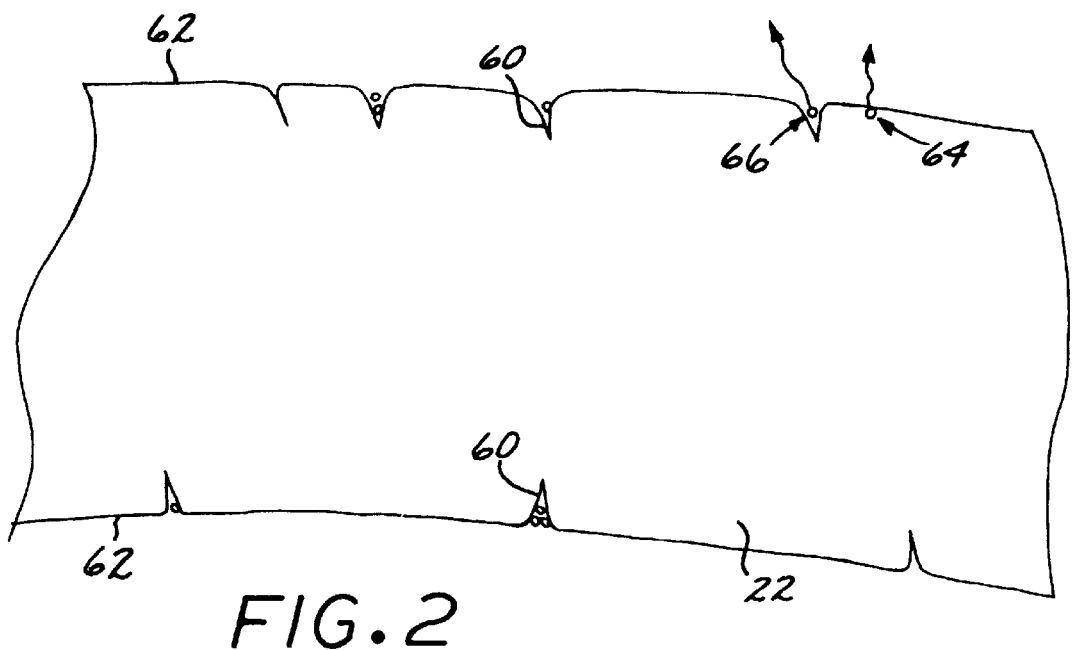
FIG. 2 is a schematic enlarged sectional view of an elastomeric article.

The cleaning agent, in conjunction with the procedures described herein, is operable to dislodge a particulate contaminant from the elastomeric article 22 and to entrain the particulate contaminant in the gaseous flow as it passes by the elastomeric article 22. FIG. 2 schematically illustrates a section through the elastomeric article 22. During storage, shipment, and use, elastomeric articles 22 typically develop small microcracks 60 at the surfaces 62 thereof. Such microcracks 60 are found in both natural latex and synthetic elastomers. These microcracks 60 are not so large and deep as to cause the elastomeric article 22 to fail, and the microcracks 60 are therefore acceptable in many uses of the articles.

However, the surface microcracking of the elastomeric article 22 can lead to the production or retention of particulate material which can later fall from the article and lead to particulate-contamination problems in some environments, such as a clean room manufacturing environment or some medical environments. Some particulate is produced as the elastomeric material itself breaks away (spalls) from the surface 62, as illustrated at numeral 64. Some particulate is also produced by particles that arise externally being entrapped and retained within the microcracks 60 as the user flexes the article, and then being released later to fall away from the elastomeric article 22, as illustrated at numeral 66.

The cleaning agent preferably includes a nebulizer (vaporizer) source 40 of a vaporized cleaning material, which is supplied through a source feed 42. The nebulizer source 40 creates fine particles of vaporized cleaning material, preferably from about 20 micrometers to about 50 micrometers in diameter. The nebulizer source 40 preferably is a low-pressure, low-volume ultrasonic nebulizer, such as the commercially available Model XL6040 made by Misonix, Inc. The ultrasonic energy introduced by this type of nebulizer source also aids in dissociation of the molecules of the vaporized cleaning material, and lowers the electromagnetic energy required to achieve ionization of the molecules. The nebulizer source 40 may instead be a high-pressure, low-volume spray head that establishes ultrasonic waves in the vaporized cleaning material, leading to a higher dissociation and subsequent ionic activity.

The cleaning agent is preferably a liquid that flows through the source feed 42, and then vaporizes as it flows from the nebulizer source 40. Preferred cleaning agents include aqueous solutions of ethylenediaminetetraacetate (sometimes abbreviated EDTA), isopropyl alcohol (sometimes abbreviated IPA), oxalic acid, and hydrogen peroxide. Intake air flows into the enclosure 24 through an intake pipe 44 and the intake port 34. The intake air first passes through a filter 46, such as a 0.5 micrometer particle filter, and then past the nebulizer source 40. The vaporized cleaning material vaporized by the nebulizer source 40 is entrained in the intake air flow, and thence flows into the interior 28 of the enclosure 24.

The source 38 also includes a weakly ionized plasma source 48 disposed within the interior 28 of the enclosure 24 and proximate to the article support location 32 to create a weakly ionized plasma in the ambient atmosphere adjacent to the article support location 32 and thence to the elastomeric article 22. The weakly ionized plasma has a temperature of not greater than 120° F., does not exceed 5 percent ions, and has a recombination time which does not exceed 10 seconds. The weakly ionized plasma source includes the vaporized cleaning agent flowing from the nebulizer source 40, and an ionization source that excites the vaporized cleaning agent. The preferred ionization source is a set of electrodes 49 contacting the vaporized cleaning agent. The ionization electrodes 49 are energized by an AC, a DC, or a pulsed DC voltage sufficient to create a weakly ionized plasma in the vaporized cleaning agent. The ionization electrodes 49 are depicted as plates positioned around the article 22, but they may have other operable forms and locations. For example, the ionization electrodes may be in a point, bar, ring, strip, or coil form, and may instead be positioned at the intake port 34, at the intake port 34 and after the vaporized cleaning agent has passed the article 22, or as a ring around the interior circumference of the enclosure 24. The ionization voltage relative to the ground plate applied through the ionization electrodes 49 is preferably about 1000 volts or less. The ionization energy may instead be provided by ultraviolet light, preferably operating in the long wavelength range of about 365 nanometers (nm), the mid wavelength range of about 302 nm, or the short wavelength range of about 254 nm. The intensity of the ultraviolet light is preferably in the range of 720–2250 microwatts per square centimeter, measured at distance of 3 inches from the source. The air flow and ionizing functions may also be combined and supplied by an ionizing air blower or in-line ionizer, such as those available commercially from ElectroStatics, Inc., Harleysville, Pa. or Ion Systems, Berkeley, Calif.

The combined action of the vaporized cleaning material and the weakly ionized plasma, as well as the pressure pulsing of the article, surrounding the elastomeric article 22 causes particles to dislodge from the microcracks 60 and the surfaces 62 of the elastomeric article 22, as schematically illustrated in FIG. 2. The dislodged particles become entrained in the flow of gas from the intake port 34 toward the exhaust port 36, and flow into an exhaust pipe 50. A fan 52 in the exhaust pipe 50 provides the pressure differential to create the gas flow from the intake port 34 to the exhaust port 36, which is typically from about 20 liters per second to about 80 liters per second for an area of the intake port 34 of about 144 square inches.

A particle counter 54 measures the particles in the gaseous flow after the gas flow has passed by the elastomeric article 50. Preferably, the particle counter 54 is located within the exhaust pipe 50, to ensure counting of all of the particles entrained in the gas flow, but it may be positioned so that the gas flow passes the particle counter before the gas flow enters the exhaust port 36. The particle counter 54 may be of any operable type. The particle counter 54 desirably gives particle counts in real time. Preferably, the particle counter 54 is a laser particle counter. Such laser particle counters are known in the art, and are available commercially from Climet Instruments and the Met One Division of Pacific Scientific, for example. Other types of particle counters, such as white light particle counters or air filter systems, may also be used but are less preferred.

Figure 3:
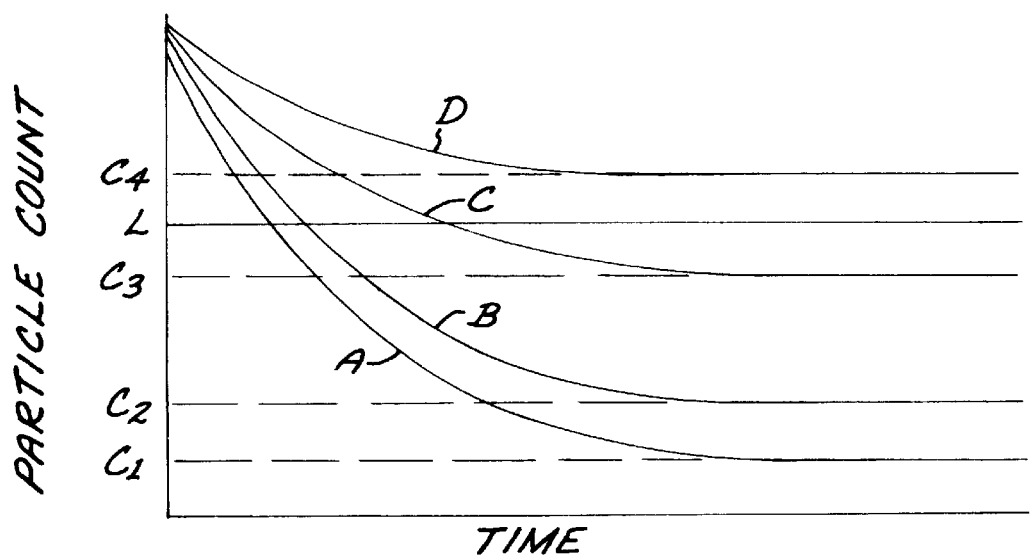
FIG. 3 is a schematic graph of particle count as a function of time.

FIG. 3 illustrates idealized curves of particle count as a function of time for an elastomeric glove tested using the present approach. In a first test indicated by curve A, the particle count is reduced from a high value to a low value that becomes asymptotic to a limiting value $C_1$ in about 3–5 seconds. The initial particle count of the glove before cleaning and the particle count reduction as a function of time are available from curve A. A line L is indicated in FIG. 3 as the limiting value that the limiting value must lie below for the glove to be acceptable for re-use in service. In this case, $C_1$ lies below L, and the glove may be reused.

If the glove is placed back into service and later tested, a curve B and limiting value $C_2$ are observed. For each retest, the particle count curve typically lies above the particle count curve for the prior test. In this case, curve B lies above curve A. In this example, the value of $C_2$ lies below L, and the glove may be re-used in service. The glove is again re-used in service and tested, and a curve C results lying above curve B, with a limiting value $C_3$ that is also below L so that the glove may be re-used again.

The glove is re-used and re-tested, and a curve D results lying above curve C, having a limiting value $C_4$ that lies above L. At this point, the glove may not be re-used, and the worker is required to discard that glove and don another glove. However, the present test and cleaning procedure allowed the glove to be re-used several times before discarding, a great improvement over the conventional approach of donning a new glove on a regular basis.

The value of L may be established in any of several ways. It may be established by a standard. It may also be established by correlating the limiting values $C_1$ with manufacturing performance. For example, higher values of $C_1$ indicate that greater particulate contents remain on the glove, and these contents may be correlated with reduced manufacturing device yields due to contamination. Studies may be conducted to establish the level L at which reduced costs due to re-use of gloves and lower worker down-time result in decreased product yields in manufacturing.

The present approach may be contrasted with that of prior particle measurement procedures. In the RP-5 destructive test as defined by the Institute of Environmental Sciences, the glove is submerged in 750 milliliters of 0.5 micrometer-filtered water held in a 2000 milliliter beaker. The beaker is mixed on an orbital mixer for 10 minutes. The glove is removed, and the water is run through a laser liquid particle counter to obtain a particle count. This test leaves the glove wet inside and out so that it cannot be reused and must discarded. In the Helmke drum test, the gloves are placed into a perforated stainless steel drum having a diameter of about 17 inches and a depth of about 13 inches. The drum is rotated at 10 rpm (revolutions per minute) while ultraclean air (HEPA filtered) is flushed through the drum. The air that exits the drum is run through an airborne particle counter to count the number of particles per cubic foot of air. The checks are performed on a periodic basis, for example every minute. The Helmke test is often considered a more representative test, since the glove is not immersed in water. The Helmke test allows the development of a curve of particle shedding over time. The Helmke test has important practical disadvantages, including physical abrasion of the article and its questionable effects and accuracy when applied to non-permeable material such as rubber. (The Helmke procedure is primarily used to test the shedding of clean room fabrics such as garments and wipers, not elastomeric articles.) Further, the Helmke drum test can generate significant amounts of triboelectric charging, which can cause inaccurate particle data.

Figure 4:
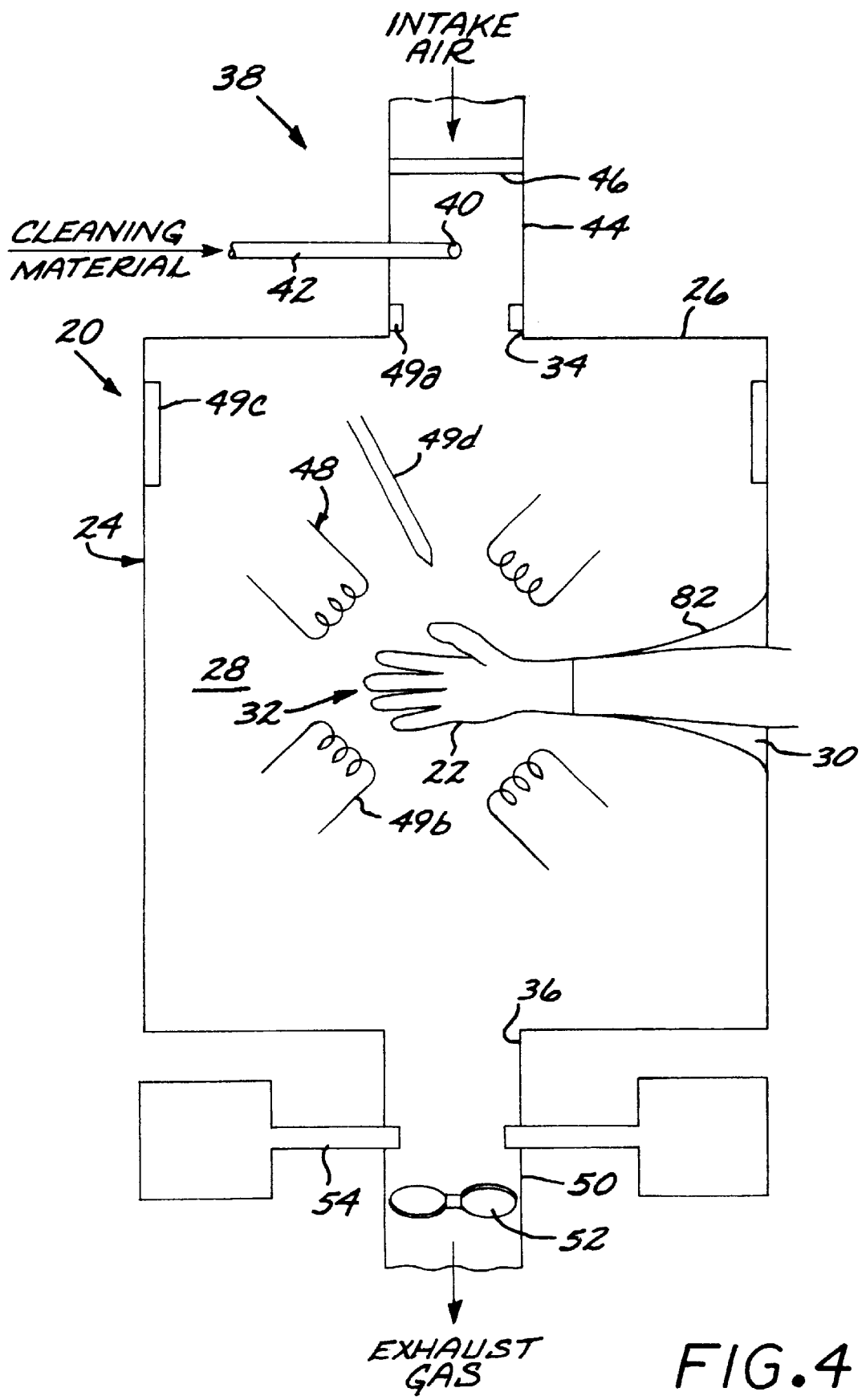
FIG. 4 is a schematic depiction of an apparatus according to a second embodiment of the invention.

The embodiment of FIG. 1 illustrated a case where the glove article is removed from the hand of the user and placed on the skeleton 70 for testing. FIG. 4 illustrates another embodiment where the user continues to wear the glove during particle measurement and glove cleaning. Many of the elements described in relation to FIG. 4 are the same as in FIG. 1. For those elements, the same reference numerals are used in the embodiment of FIG. 4, and the earlier description is incorporated by reference.

The primary difference in the embodiment of FIG. 4 from that of FIG. 1 is that the user continues to wear the glove during the testing. The user thrusts the hand wearing the glove through a gland 82 in the access port 76, so that the glove article is in the article support location 32. The gland and the rim of the access port 76 serve as the support 30, together with the hand and arm of the user. The gland 82 need not provide a hermetic seal or even a tight seal, because the pressure differential between the environment outside of the enclosure 24 and in the interior 28 of the enclosure 24 is small.

The embodiment of FIG. 4 illustrates an important advantage of using the weakly ionized plasma sources 48 described above, rather than conventional high-energy plasmas. The user may thrust his hand, protected only by the thin glove article, directly into the weakly ionized plasma produced by the sources 48, which is not generally possible where high-energy sources are used. The ionization electrodes 49 are illustrated in FIG. 4 in several different forms from the electrodes of FIG. 1, although in practice only one type of ionization electrode would normally be used at any time. Such ionization electrodes 49 include electrodes 49a at the point of entry 34 of the vaporized cleaning material, filament electrodes 49b adjacent to the article support location 32, a ring electrode 49c extending around the circumference of the enclosure 24, and a point electrode 49d.

Figure 5:
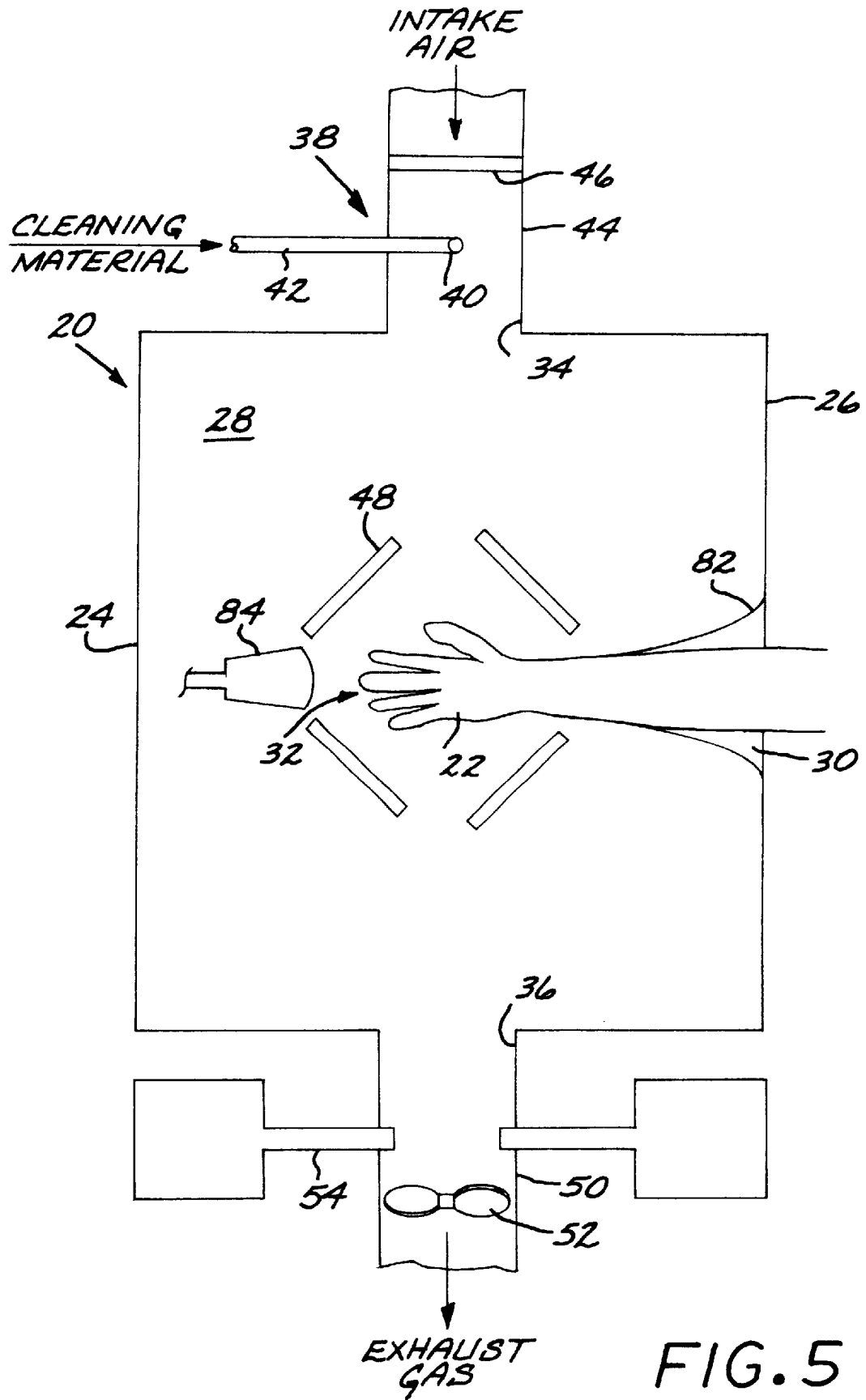
FIG. 5 is a schematic depiction of an apparatus according to a third embodiment of the invention.

The embodiments of FIGS. 1 and 4 are operable to measure and reduce particulate matter on the glove, a key concern in applications such as clean rooms. Some other applications, such as medical facilities including hospitals, doctor's offices, and dental offices, require that the glove be sterilized of microorganisms as well. FIG. 5 illustrates an embodiment of the invention which measures and cleans the gloves of particulate, and simultaneously sterilizes the glove of microorganisms present on its outer surface. Many of the elements described in relation to FIG. 5 are the same as in FIGS. 1 and 4. For those elements, the same reference numerals are used in the embodiment of FIG. 5, and the earlier description of FIGS. 1 and 4 is incorporated by reference.

In this case, the user wears the glove as in the embodiment of FIG. 4. A microorganism sterilizer is disposed within the interior 28 of the enclosure 24, proximate to the article support location 32. The microorganism sterilizer may be of any operable type that is compatible with the particle measurement and cleaning apparatus, such as an illustrated UV (ultraviolet) lamp 84. Suitable UV lamps are available commercially from Aqua Ultraviolet USA. The microorganism sterilizer may be of other types as well, such as an ozone source, or a sterilizing gas introduced through the nebulizer source 40 or separately. Another form of sterilization may be accomplished by selection of the vaporized cleaning material. If hydrogen peroxide ($H_2O_2$) is used as the vaporized cleaning material, the ionizing energy of the weakly ionized plasma causes the molecules to dissociate to water and monatomic oxygen, which is reactive to oxidize organic contaminants. The use of an ultrasonic nebulizer facilitates the dissociation.

The microorganism sterilization may be accomplished either before, simultaneously with, or after the particulate measurement and cleaning. This embodiment of FIG. 5 allows personnel in medical facilities to re-use gloves in an appropriate manner. Typically, gloves might be reused for multiple procedures with the same patient or procedure, but not reused with different patients. Nevertheless, the present approach would provide an increase in safety to prevent contamination, and an increase in efficiency through decreased glove disposal.

Figure 6:
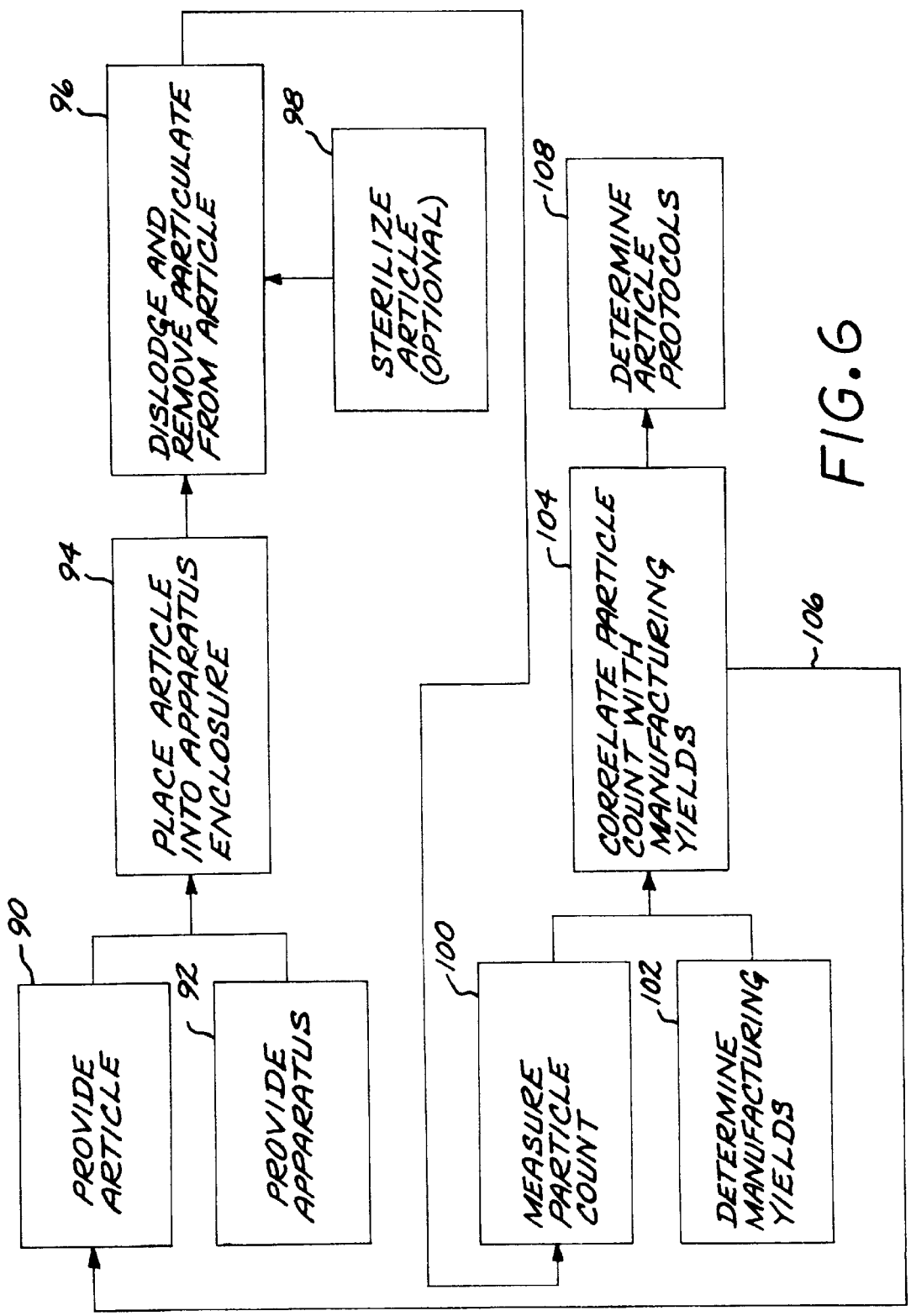
FIG. 6 is a block diagram of a method for practicing the invention.

FIG. 6 illustrates a preferred approach for practicing the invention. It is presented in a general form to address a wide variety of possible applications of the present invention. The above discussion is incorporated by reference as to FIG. 6. The article 22 to be cleaned is provided, numeral 90. An operable apparatus to accomplish the cleaning is provided, numeral 92, such as the apparatus 20 described above. The article 22 is placed into the apparatus 20, numeral 94. The apparatus 20 is operated, numeral 96, to dislodge and remove the particulate from the article. Where appropriate, as in medical and laboratory facilities, the article 22 may also be sterilized, numeral 98. The particle count for the article 22 is measured using the particle counter 54, numeral 100. The steps 96/98 and 100 are typically performed simultaneously, so that the particle count is measured as a function of time, from the start of cleaning to the end of cleaning as depicted in the graphs of FIG. 3. The particle count may be correlated with another quantity. For example, in a clean room manufacturing operation the manufacturing yields are determined, numeral 102, typically by establishing the fraction of operable products as a function of the attempted products. The particle count information from step 100, together with related information gathered with the particle count information, such as time of cleaning, frequency of cleanings, and number of times each article is reused before discarding, is correlated with the manufacturing yields, numeral 104. These steps 90–104 are typically repeated each time an article is cleaned, to gather a body of data, as indicated by the recursive loop 106. The correlations from step 104 are used to determine article cleaning protocols, numeral 108, such as frequency of cleanings and number of times an article may be reused before it must be discarded.

Within the general approach of FIG. 6, there may be numerous variations according to the specific circumstances.

For example, in a clean room manufacturing environment, the order of steps 96/98, 100, and 104 may be varied and/or the steps may be repeated in various arrangements. Continuing experience with the practice of the present invention in a particular clean room setting will aid in establishing the variables which correlate with manufacturing yields, because at the present time the existing techniques cannot be used to make such correlations. In another variation, after testing with the present approach a selected group of the articles may be tested with other procedures, such as the RP-5 test or the Helmke test, to establish a correlation between the results attained with present approach (which allows reuse of the articles) and the results attained with these other testing approaches (which do not allow reuse of the articles).

In another variation of the approach of FIG. 6, in a medical office, operating room, or laboratory setting, steps 102, 104, and 108 may be omitted, and articles may be cleaned several times before discarding. Typically, the article can be reused only as long as the article is used with a single patient, and not with multiple patients. Even in these environments, correlation procedures may be desirably applied.

Many other variations of the basic approach of FIG. 6 are possible. The present invention may be viewed as both a measuring and cleaning/sterilizing technique, and also a tool to gather information used to improve practices.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. Apparatus for processing an elastomeric article, comprising:
    an enclosure having a gas-filled interior and an access port with a non-hermetic gland seal therein sized so that a person wearing the elastomeric article may insert a hand and an arm through the gland to position the elastomeric article at an article support location;
    a source of an ionized gaseous cleaning agent operable to produce an ionized gaseous flow of the gaseous cleaning agent that flows past the article support location and contacts the elastomeric article, the ionized gaseous cleaning agent being operable to dislodge a particulate contaminant from the elastomeric article and entrain the particulate contaminant in the gaseous flow as it passes by the elastomeric article; and
    an exhaust port positioned to receive the gaseous flow after it has passed by the elastomeric article.

2. The apparatus of claim 1, further including
    a particle counter that measures particles in the gaseous flow after it has passed by the elastomeric article.

3. The apparatus of claim 1, wherein the elastomeric article is a glove.

4. The apparatus of claim 1, further including
    an elastomeric article in the form of a glove.

5. The apparatus of claim 1, wherein the source of the gaseous cleaning agent comprises:
    a source of a vaporized cleaning material, and
    a weakly ionized plasma source disposed within the interior of the enclosure and proximate to the article support location to create a weakly ionized plasma in the ambient atmosphere adjacent to the article support location.

6. The apparatus of claim 5, wherein the cleaning material comprises a material selected from the group consisting of ethylenediaminetetraacetate, isopropyl alcohol, oxalic acid, and hydrogen peroxide.

7. The apparatus of claim 1, further including
    a microorganism sterilizer disposed within the interior of the enclosure and proximate to the article support location.

8. Apparatus for processing an elastomeric article in the form of a glove, comprising:
    an enclosure having a gas-filled interior;
    a support that supports the glove within the enclosure at an article support location, wherein the support comprises
    a form that receives the glove thereon, and
    a source of gaseous pressure to inflate the glove on the form;
    a source of a gaseous cleaning agent operable to introduce a gaseous flow of the gaseous cleaning agent into the interior of the enclosure to flow past the article support location and to contact the glove, the cleaning agent being operable to dislodge a particulate contaminant from the glove and entrain the particulate contaminant in the gaseous flow as it passes by the glove, wherein the source of the gaseous cleaning agent comprises
    a nebulizer source of a vaporized cleaning material, and
    a weakly ionized plasma source disposed within the interior of the enclosure and proximate to the article support location to create a weakly ionized plasma in the ambient atmosphere adjacent to the article support location;
    an exhaust port positioned to receive the gaseous flow after it has passed by the glove; and
    a particle counter that monitors the particles in the gaseous flow after it has passed by the glove.

9. The apparatus of claim 8, wherein the source of gaseous pressure is a pulsing source of gaseous pressure.

10. Apparatus for processing an elastomeric article in the form of a glove, comprising:
    an enclosure having a gas-filled interior, the enclosure having a gland seal therethrough;
    a support that supports the glove within the enclosure at an article support location, the support comprising a human hand and arm extending through the gland seal and upon which the glove is worn;
    a source of a gaseous cleaning agent operable to introduce a gaseous flow of the gaseous cleaning agent into the interior of the enclosure to flow past the glove and to contact the glove, the cleaning agent being operable to dislodge a particulate contaminant from the glove and entrain the particulate contaminant in the gaseous flow as it passes by the glove, wherein the source of the gaseous cleaning agent comprises
    a nebulizer source of a vaporized cleaning material, and
    a plasma source disposed within the interior of the enclosure and proximate to the article support location to create a weakly ionized plasma in the ambient atmosphere adjacent to the glove;
    an exhaust port positioned to receive the gaseous flow after it has passed by the glove; and
    a particle counter that monitors the particles in the gaseous flow after it has passed by the glove.

11. The apparatus of claim 8, wherein the cleaning material comprises a material selected from the group consisting of ethylenediaminetetraacetate, isopropyl alcohol, oxalic acid, and hydrogen peroxide.

12. The apparatus of claim 8, further including
a microorganism sterilizer disposed within the interior of the enclosure and proximate to the article support location.

13. Apparatus for processing an elastomeric article, comprising:
an enclosure having a gas-filled interior;
a support that receives the elastomeric article thereon and supports the elastomeric article within the enclosure at an article support location, wherein the article support comprises
a form that receives the elastomeric article thereon, and
a source of pulsing gaseous pressure to inflate the elastomeric article on the form;
a source of a gaseous cleaning agent operable to introduce a gaseous flow of the gaseous cleaning agent into the interior of the enclosure to contact the elastomeric article, the cleaning agent being operable to dislodge a particulate contaminant from the elastomeric article and entrain the particulate contaminant in the gaseous flow as it passes by the elastomeric article, wherein the source of the gaseous cleaning agent comprises
a nebulizer source of a vaporized cleaning material, and
a weakly ionized plasma source disposed within the interior of the enclosure and proximate to the article support location to create a weakly ionized plasma in the ambient atmosphere adjacent to the article support location;
an exhaust port positioned to receive the gaseous flow after it has passed by the elastomeric article; and
a particle counter that monitors the particles in the gaseous flow after it has passed through the exhaust port.

14. The apparatus of claim 13, further including
an elastomeric article in the form of a glove.

15. The apparatus of claim 13, wherein the cleaning material comprises a material selected from the group consisting of ethylenediaminetetraacetate, isopropyl alcohol, oxalic acid, and hydrogen peroxide.

16. The apparatus of claim 13, further including
a microorganism sterilizer disposed within the interior of the enclosure and proximate to the article support location.

17. A method for processing an elastomeric article in the form of a glove, comprising the step of
supporting the glove on a form at an article support location, the glove being inflated on the form;
passing a gaseous flow of a gaseous cleaning agent to contact the elastomeric article positioned at an article support location, the cleaning agent being operable to dislodge a particulate contaminant from the elastomeric article and entrain the particulate contaminant in the gaseous flow as it passes by the elastomeric article, wherein the source of the gaseous cleaning agent comprises
a nebulizer source of a vaporized cleaning material, and
a weakly ionized plasma source disposed within the interior of the enclosure and proximate to the article support location to create a weakly ionized plasma in the ambient atmosphere adjacent to the article support location; and
measuring the particulate content of the gaseous flow after it has passed by the elastomeric article.

18. The method of claim 17, including an additional step, after the step of measuring, of
correlating the measured particulate content with another quantity.

19. The apparatus of claim 8, wherein the source of gaseous pressure is a pulsing source of gaseous pressure.

20. The apparatus of claim 1, wherein the source of the ionized gaseous cleaning agent comprises:
a source of a vaporized cleaning material, and
a plasma source operable to ionize the vaporized cleaning material.

* * * * *